United States Patent [19]

Higo et al.

[11] 4,162,258

[45] Jul. 24, 1979

[54] NOVEL COMPOUNDS SPIRO[5-ISOPROPYLBICYCLO[3.1.0]HEXANE-2,2'-OXIRANES], PROCESS FOR THE PRODUCTION OF THE NOVEL COMPOUNDS, AND PROCESS FOR THE PRODUCTION OF SABINENE HYDRATES THEREFROM

[75] Inventors: Moriaki Higo, Hiratsuka; Haruhiko Toda, Minami-ashigara; Kunitomo Suzuki, Yamanishi; Yasukuni Nishida, Odawara, all of Japan

[73] Assignee: The Lion Dentifrice Co., Ltd., Tokyo, Japan

[21] Appl. No.: 890,337

[22] Filed: Mar. 27, 1978

[30] Foreign Application Priority Data

| Apr. 6, 1977 | [JP] | Japan | 52/39199 |
| Jun. 6, 1977 | [JP] | Japan | 52/66567 |
| Jun. 6, 1977 | [JP] | Japan | 52/66568 |
| Jun. 16, 1977 | [JP] | Japan | 52/71396 |
| Sep. 29, 1977 | [JP] | Japan | 52/117160 |

[51] Int. Cl.$^2$ .................................. C07D 303/04
[52] U.S. Cl. .................. 260/348.11; 252/522; 568/819
[58] Field of Search .................................. 260/348.11

*Primary Examiner*—Norma S. Milestone
*Attorney, Agent, or Firm*—Ladas, Parry, Von Gehr, Goldsmith & Deschamps

[57] ABSTRACT

Novel compounds trans- and/or cis-spiro[5-isopropylbicyclo[3.1.0]hexane-2,2'-oxiranes], process for the production of the novel compounds comprising reacting 3-isopropyl-2-cyclopenten-1-one with sulfoxonium methylide to form the novel compounds, process for the production of novel compounds comprising reacting 5-isopropylbicyclo[3.1.0]hexan-2-one with sulfonium methylide or sulfoxonium methylide to form the novel compounds, and process for the production of novel compounds comprising the steps of reacting 3-isopropyl-2-cyclopenten-1-one with sulfoxonium methylide to form 5-isopropylbicyclo[3.1.0]hexan-2-one and then reacting the 5-isopropylbicyclo[3.1.0]hexan-2-one with sulfonium methylide or sulfoxonium methylide to form the novel compounds. Trans- and/or cis-sabinene hydrates can readily be prepared from the novel compounds trans- and/or cis-spiro[5-isopropylbicyclo[3.1.0]hexane-2,2'-oxiranes].

3 Claims, No Drawings

NOVEL COMPOUNDS SPIRO[5-ISOPROPYLBICYCLO[3.1.0]HEXANE-2,2'-OXIRANES], PROCESS FOR THE PRODUCTION OF THE NOVEL COMPOUNDS, AND PROCESS FOR THE PRODUCTION OF SABINENE HYDRATES THEREFROM

BACKGROUND OF THE INVENTION

The present invention relates to novel compounds spiro[5-isopropylbicyclo[3.1.0]hexane-2,2'-oxiranes], which were found to be useful not only as important intermediates for producing valuable compounds such as trans-sabinene hydrate utilized as an intensifier for spearmint type flavor or peppermint type flavor, but also per se as perfumes or flavors and moreover as constituents of perfume or flavor compositions, and to processes for producing said novel compounds as well as to a process for producing sabinene hydrates therefrom. More particularly, the present invention relates to the novel compound trans-spiro[5-isopropylbicyclo[3.1.0]hexane-2,2'-oxirane] having the formula (1)

(1)

as well as to another novel compound cis-spiro[5-isopropylbicyclo[3.1.0]hexane-2,2'-oxirane] having the formula (2)

(2)

, and further to a process for producing these novel compounds from 5-isopropylbicyclo[3.1.0]hexan-2-one and to another process for producing said novel compounds from 3-isopropyl-2-cyclopenten-1-one as well as process for producing trans- and/or cis-sabinene hydrates by reducing said compounds with a reducing agent.

trans- and cis-Sabinene hydrates have hitherto been attracted an attention for flavor components for dentifrice, foods and drinks etc. In particular, the trans-sabinene hydrate, which is widely contained in essential oils such as peppermint oil and spearmint oil in an amount of about 1% (for example, it is contained in the essential oil *Menta piperita L.* in an amount of 0.8%) and in some cases even up to about several %, has specifically been noticed as an intensifier for the peppermint type flavor or spearmint type flavor.

DESCRIPTION OF THE PRIOR ART

U.S. Pat. No. 3,591,643 granted to W. I. Fanta et al. has disclosed a process for producing trans-sabinene hydrate and/or cis-sabinene hydrate having the structural formulae (7), (8) respectively. The process comprises four steps, i.e., (i) reduction of 3-isopropyl-2-cyclopenten-1-one having structural formula (3) as the starting material with lithium aluminum hydride in ether to obtain 3-isopropyl-2-cyclopenten-1-ol having structural formula (4), (ii) reaction of the 3-isopropyl-2-cyclopenten-1-ol with methylene iodide in the presence of zinc-copper catalyst in ether to form 5-isopropylbicyclo[3.1.0]hexan-2-ol having structural formula (5), (iii) oxidation of the 5-isopropylbicyclo[3.1.0]-hexan-2-ol with chromic acid to form 5-isopropylbicyclo[3.1.0]hexan-2-one having the structural formula (6) (hereinafter referred to as sabina ketone), and (iv) reaction of the sabine ketone with methyl magnesium bromide etc. or with methyl lithium to produce trans-sabinene hydrate and/or cis-sabinene hydrate having the structural formulae (7), (8) respectively. The reaction sequence A may be schematically represented as follows:

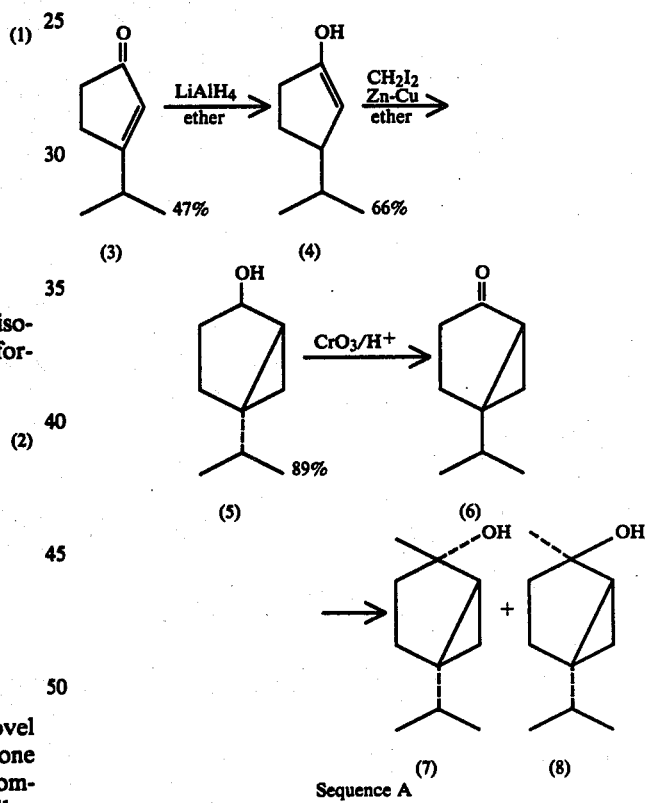

Sequence A

In the process, however, a relatively greater number of steps have to be pursued up to the course of synthesis of sabina ketone (6). In addition, since sabine ketone is obtainable from the starting material 3-isopropyl-2-cyclopenten-1-one only in about 57% yield, the total yield of sabinene hydrate results in lower value. Moreover, according to the process, operations and works are complicated and laborious, as it requires isolation procedures for each intermediate. Further, it is necessary to use valuable reagents and chromate compound hazardous in handling. Therefore, sabinene hydrates cannot be produced efficiently or economically, in particular, in large scale. Furthermore, by the process, cis-sabinene hydrate (formula 8) is produced preferentially and trans-sabinene hydrate (formula 7) appears only in a considerably minor amount. That is to say, a ratio of formation of trans-compound to cis-compound is 1:8.5, so that the process does not suit an industrial synthesis of trans-sabinene hydrate. Also, yield of trans- and cis-sabinene hydrates from sabina ketone is about 11%, and yield from 3-isopropyl-2-cyclopenten-1-one is about 6.3%.

Since the trans-compound cannot be produced in a higher yield by methylating sabina ketone, it has heretofore been forced to follow such a course to synthesize the trans-compound as shown in the following sequence B:

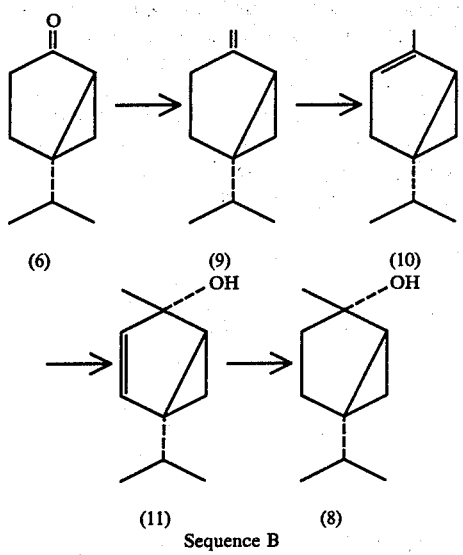

Sequence B

At first, sabina ketone is reacted with methylenetriphenylphosphorane to form sabinene having structural formula (9) [refer to U.S. Pat. No. 3,591,643 as well as to O. P. Vig et al., J. Indian Chem. Soc., 46, 991 (1969)], this compound (9) is then reacted with potassium tert-butoxide in dimethyl sulfoxide to produce α-thujene having structural formula (10) [refer to S. P. Acharya et al., J. Org. Chem., 34, 3015 (1969)], this α-thujene is then subjected to photo oxygenation to give trans-2-thujen-4-ol having structural formula (11), and the so obtained material (11) is converted to trans-sabinene hydrate (7) by hydrogenation using metal catalyst [refer to G. Ohloff et al., Tetrahedron, 22, 309 (1966)].

However, such a process according to sequence B requires four steps, i.e. a Wittig reaction, isomerization using a strong alkali, photo oxygenation and hydrogenation in the presence of a metal catalyst. Therefore, seven steps are necessary for the total course starting from the compound (3), so that considerably complicated procedures should be endured and trans-sabinene hydrate cannot be synthesized in a simple manner. Moreover, since the total yield of trans-sabinene hydrate from sabina ketone in the above four steps amounts to about 44%, the over-all yield starting from the compound (3) will amount to about 25%. Thus, this process does not operate efficiently, so that it is requested to establish a novel process for producing trans-sabinene hydrate in a simple manner in higher yield. At the same time, it has also been requested to find out a novel process, wherein cis-sabinene hydrate which is also useful as a flavor constituent etc. can be synthesized in an easier manner.

SUMMARY OF THE INVENTION

Therefore, it is a primary object of the present invention to provide novel compounds which are useful not only as intermediate for sabinene hydrates etc., but also per se as flavors or perfumes and as components for flavor perfume compositions.

The second object of the present invention is to provide processes for preparing spiro[5-isopropylbicyclo[3.1.0]-hexane-2,2'-oxiranes], wherein both trans- and cis-isomers can be produced under a mild condition without severe conditions such as high temperature and high pressure in substantially no furmation of by-products and wherein the trans-isomer can be formed preferentially, while at the same time the cis-isomer can also be produced easily.

The third object of the present invention is to provide a process for producing the trans- and cis-sabinene hydrates in a reliable and easier manner from said novel compounds trans- and cis-spiro[5-isopropylbicyclo[3.1.0]hexane-2,2'-oxiranes].

Other objects and advantages of the present invention will be apparent to those skilled in the art from the following descriptions.

According to the present invention, there are provided novel compounds trans- and cis-spiro[5-isopropylbicyclo[3.1.0]hexane-2,2'-oxiranes] as mentioned above.

According to the present invention, there are further proposed (i) a process for producing spiro[5-isopropylbicyclo[3.1.0]hexane-2,2'-oxiranes] comprising reacting 3-isopropyl-2-cyclopentan-1-one with sulfoxonium methylide in an amount ratio of 2 moles or more of the latter per 1 mole of the former to produce directly said novel spiro compounds, (ii) another process for producing said novel spiro compounds comprising reacting 5-isopropylbicyclo[3.1.0]-hexan-2-one with sulfonium methylide or with sulfoxonium methylide, (iii) still another process for producing said novel spiro compounds comprising reacting 3-isopropyl-2-cyclopentan-1-one with sulfoxonium methylide in an amount ratio of less than 2 moles of the latter per 1 mole of the former to form 5-isopropylbicyclo[3.1.0]hexan-2-one and then reacting the so obtained 5-isopropylbicyclo[3.1.0]hexan-2-one with either an amount of sulfoxonium methylide or with an amount of sulfonium methylide, and (iv) a process for producing trans- and/or cis-sabinene hydrates comprising reducing trans- and/or cis-spiro[5-isopropylbicyclo[3.1.0]hexane-2,2'-oxiranes] with a reducing agent.

DETAILED DESCRIPTION OF THE INVENTION

The novel compounds trans- and cis-spiro[5-isopropylbicyclo[3.1.0]hexane-2,2'-oxiranes] (hereinafter referred to as "trans-sabinene oxide" and "cis-sabinene oxide" respectively) according to the present invention are represented by the structural formulae (1) and (2) as above. Both trans- and cis-sabinene oxides are presented in a liquid state at room temperature. The trans-sabinene oxide exhibits a fresh, refrigerant and lightly greenish fragrance, whereas cis-sabinene oxide has a woody, costus-like and refreshing odor resembling camphor.

Since, they have favorable fragrances, they are used each per se as perfume or flavor and as constituent of perfume or flavor formulation and may be applied widely in the perfume industry, pharmaceutical industry and the like. They are also useful for synthesizing trans- and cis-sabinene hydrates.

Thus, the trans- and cis-sabinene oxides can be blended either alone or in mixture with each other in a voluntary proportion for flavors for dentifrice, refrigerant troche, gargle, foods, chewing-gum etc., and for perfumes for cosmetics such as perfumes, cologne, eau-de-toilet, lotion, cream, hairliquid, hair-tonic, antiperspirant, shampoo, soap etc. Also, trans- and/or cis-isomers may be used for odors for household products such as room perfume, deodorant, cleaners and the like. When trans- and/or cis-isomers are formulated, refreshing and refrigerating feels may be obtained. When trans-sabinene oxide is blended especially in perfume compositions for cosmetics as a modifier, a fresh greenish fragrance with a refrigerant feeling may be obtained. Therefore, the trans-isomer may be used in perfume compositions for, perfumes, cologne, eau-de-toilet, creams, tonics, lotion and the like so as to give an odor that accentuates freshness and naturalness. Also, when the trans-isomer is incorporated into flavor compounds for dentifrice, refrigerant troche, gargle and the like, the fresh and refrigerant green note may be obtained.

When cis-sabinene oxide is used as a modifier in perfume compositions for scents, cologne, eau-de-toilet, creams, tonics, lotions etc, a fragrance accentuating the naturalness and light and refreshing feels may be obtained. When cis-isomer is incorporated in flavor compositions, a refreshing feel may be obtained and the total fragrancy is high.

Explaining more detailedly, when trans- and/or cis-sabinene oxides are blended in a spearmint type flavor composition for dentifrice, the fragrant tone of spearmint is lifted up and, at the same time, its refrigerant and refreshing feels increase. When trans- and/or cis-sabinene oxides are blended in a peppermint type flavor composition for dentifrice, the oily fragrance inherent to terpenes contained as an essential component will be reduced and a fragrant tone becomes mild, fresh and refrigerant. Also, when trans- and/or cis-sabinene oxides are incorporated in flavor compositions of jasmine floral, fantasy floral, white rose and the like, refreshing and fresh feeling and accentuated naturalness may be obtained.

The amount of trans- and/or cis-sabinene oxides to be blended may vary depending upon the type of flavor composition, specific odor to be expected, and the finished products etc. trans- and/or cis-Sabinene oxides may be used in an amount between 0.001% and 45% by weight, preferably 0.01 to 15% by weight based on the weight of the flavor composition. For trans-sabinene oxide, an amount to be used is between 0.001% and 30% by weight, preferably, 0.01 to 15% by weight.

trans- and/or cis-Sabinene oxides can be blended in every known flavor and perfume compositions. The trans- and/or cis-Sabinene oxides may be formulated in conventional manner. trans- and cis-Sabinene oxides are easily soluble in solvents such as ethanol and are stable in acids and alkalis, so that they do not require special blending operation on blending them. The trans- and cis-Sabinene oxides exhibit no greater toxicity. When these compounds are used in a food flavor, the amount of these compounds may be a little, therefore no problem occurs in safety.

In one embodiment of the process for producing trans- and cis-sabinene oxides, 3-isopropyl-2-cyclopenten-1-one having structural formula (3) is reacted with sulfoxonium methylide in an amount of 0.5–2 moles of the latter per one mole of the former to form sabina ketone having structural formula (6), and then the so obtained sabina ketone (6) is reacted with sulfonium methylide or with sulfoxonium methylide. The reaction sequence C may be schematically represented as follows:

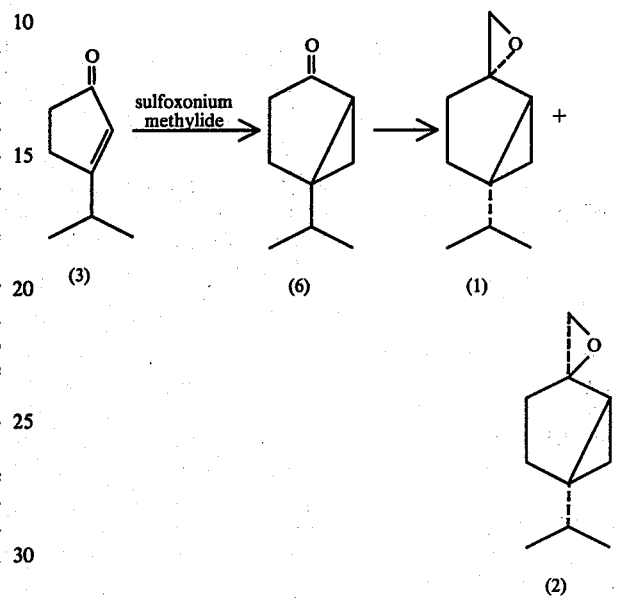

Sequence C

The trans- and cis-sabinene oxides can also be prepared by reacting directly the sabina ketone obtained, for example, by the process according to U.S. Pat. No. 3,591,643 with sulfonium methylide or sulfoxonium methylide.

In another embodiment of the process for producing trans- and cis-sabinene oxides, 3-isopropyl-2-cyclopentan-1-one (3) is reacted with sulfoxonium methylide in a molar ratio of 2–5 moles of the latter per 1 mole of the former. The reaction sequence D may be schematically represented as follows:

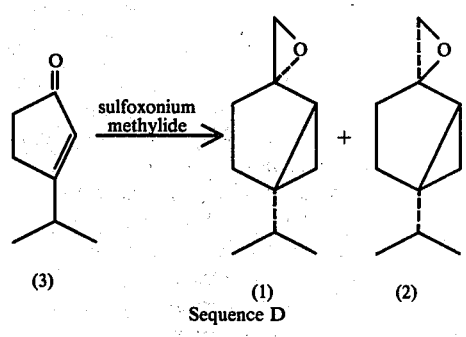

Sequence D

Here, 3-isopropyl-2-cyclopentan-1-one having structural formula (3) can be synthesized, for example, by reacting 6-methyl-2,5-heptanedione with a base (refer to U.S. Pat. No. 3,591,643).

Sulfonium methylide and sulfoxonium methylide which are employed in the processes sequences C and D can be obtained by reacting a base either with the corresponding methyl sulfonium salt having the general formula (12)

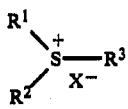
(12)

or with the corresponding methyl sulfoxonium salt having the general formula (13).

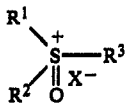
(13)

Wherein $R^1$ and $R^2$ represent each alkyl groups such as methyl, ethyl, propyl or tert-butyl group, aromatic groups such as phenyl, substituted phenyl or naphthyl group, aralkyl groups, alkylene groups or substituted alkylene groups formed by combining $R^1$ with $R^2$, or alkyl amino groups such as diethylamino group, and $R^3$ represents methyl group in which one or more of hydrogen atoms can be substituted by atoms or atomic groups such as halogen, silicon group or sulfur group. Therefore, the methyl sulfonium salt and methyl sulfoxonium salt to be used according to the present invention represent those compounds which are indicated by the formulae (12) and (13) wherein $R^3$ represents a methyl group or a substituted methyl group. Thus, sulfonium methylide and sufoxonium methylide used in the present invention can be represented by the formulae.

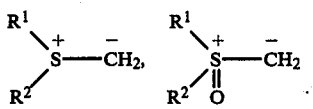

At least one hydrogen in the $-\bar{C}H_2$ group of the above formulae may be substituted by one or more atoms or atomic groups such as halogen, silicon group or sulfur group. When the methylide is derived from a salt of methyl sulfonium or methyl sulfoxonium in which $R^3$ in the above formula (12) or (13) represents a substituted methyl group, after it is reacted with sabina ketone or 3-isopropyl-2-cyclopentan-1-one of structure (3), it is necessary to remove the substituent atom or group from the product.

In the above structural formulae (12) and (13), $X^-$ represents an anion such as halogen, borofluoride, chlorate, perchlorate, hexachloroantimonate, picrate, sulfonate, sulfate, sulfate ester, nitrate or tetraphenylborate ion. In many cases, halogen ion, borofluoride ion or sulfate ester ion may be employed therefor.

The base to be reacted with the methyl sulfonium salt or methyl sulfoxonium salt (there are referred to hereinafter summarily as methyl onium salt) to obtain the methylides is as follows. Metal hydroxides such as sodium hydroxide, potassium hydroxide, calcium hydroxide etc.; metal carbonates such as sodium carbonate, potassium carbonate etc.; metal salts of acids such as sodium acetate, potassium acetate etc.; metal oxides such as silver oxide, calcium oxide etc; metal hydrides such as sodium hydride, potassium hydride, calcium hydride etc.; alcoholates such as sodium ethoxide, potassium tert-butoxide etc.; dimusyl sodium

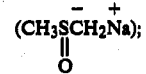

dimusyl potassium; alkyl lithiums, aryl lithiums, phenyl potassium, trityl sodium naphthalene sodium etc.; metal amides such as sodium amide, lithium amide etc.; alkali metals such as lithium, sodium or potassium; amines and quaternary ammonium salts as well as mixture thereof. Preferably, metal hydroxides, metal hydrides, alkyl lithiums, dimusyl sodium, or dimusyl potassium is employed therefor.

The methyl onium salt as defined is reacted with the base described above at a reaction temperature between −80° and 100° C., usually between −20° and 80° C. for about 1 minute to one day in a solvent described hereinafter.

When sabinene oxide is prepared by reacting sabina ketone with sulfonium methylide or sulfoxonium methylide (hereinafter referred to as "sulfur ylide") three ways may be used. In one way, after sulfur ylide is prepared by reacting the methyl onium salt with base, the sulfur ylide is purified by removing the by-product from the reaction mixutre, and thereafter purified sulfur ylide is reacted with sabina ketone in an adequate solvent. However, since sulfur ylide is unstable, following ways are preferable. In another way, the methyl onium salt is reacted with a base in an adequate solvent, and to this reaction mixture sabina ketone is then added to react with the sulfur ylide formed. In the other way, a mixture of the methyl onium salt, base and sabina ketone is reacted in an adequate solvent.

The above three ways may be used in the production of sabina ketone by reacting 1 mole of 3-isopropyl-2-cyclopenten-1-one with 0.5-2 moles of sulfoxonium methylide, and in the production of sabinene oxides by reacting 1 mole of 3-isopropyl-2-cyclopenten-1-one with 2-5 moles of sulfoxonium methylide.

The solvent used for the reaction of methyl onium salt with base may be either different or same with that used for the reaction of the sulfur ylide with 3-isopropyl-2-cyclopenten-1-one or with sabina ketone. As solvent, dimethyl sulfoxide, N,N-dimethylformamide, acetonitrile, pyridine, triethylamine, water, alcohols, tetrahydrofuran, dioxane, ethyl ether, petroleum ether, hexane, benzene, toluene, xylene, methylene chloride etc. or mixture thereof may be used. If a solvent which consists of or consists predominantly of tetrahydrofuran or which contains preferably more than 10% by weight of tetrahydrofuran is used in the reaction of sulfur ylide with sabina ketone, a reaction product in which the proportion of trans-sabinene oxide is greater than that of cis-sabinene oxide (i.e., trans-isomer to cis-isomer is 73 to 27) may be obtained, so that use of tetrahydrofuran is recommended for the purpose of obtaining the trans-isomer.

Sabina ketone is reacted with sulfur ylide at a temperature in the range of −80° C. to 100° C., preferably 0° C. to 80° C. for several minutes to two days. 3-isopropyl-2-cyclopentan-1-one is reacted with sulfoxonium methylide under the same conditions as above. Reaction may be carried out at the same temperature. Alternatively, the reaction may be effected at lower temperature, and then the reaction may be further conducted at elevated temperature to completion.

It is enough to use sulfur ylide in a stoichiometric amount, and practically an amount of 1.1 mole per 1 mole of sabina ketone may be sufficient. However, it is also possible to use the sulfur ylide in a more excessive amount so as to complete the reaction more rapidly.

In the case of synthesis of sabina ketone by the reaction of 3-isopropyl-2-cyclopenten-1-one with sulfoxonium methylide, the methylide should be used in an amount of 0.5–2 moles per 1 mole of 3-isopropyl-2-cyclopentan-1-one, and preferably, it is used in an equimolar amount or more, especially about 1.1 moles per 1 mole of 3-isopropyl-2-cyclopenten-1-one. The use of less amount of sulfoxonium methylide in this reaction will result in an incomplete reaction, whereas the use thereof in excess amount may form the sabinene oxides.

In the case of direct synthesis of sabinene oxides by the reaction of 3-isopropyl-2-cyclopenten-1-one with sulfoxonium methylide, the methylide should be used in an amount of 2–5 moles, and preferably about 2.2 moles per 1 mole of 3-isopropyl-2-cyclopenten-1-one, while it is also possible to use the methylide in an amount of about 3–5 moles per mole of said cyclopentene derivative, so as to complete the reaction within a more reduced period. Here, use of sulfoxonium methylide in a lesser amount will result in an incomplete reaction, whereas use of a greater amount offers no further advantage to the reaction.

Both the reaction mixture obtained from the reaction of sabina ketone with sulfur ylide in an adequate solvent and that obtained from the reaction of 3-isopropyl-2-cyclopenten-1-one with sulfoxonium methylide in a suitable solvent can be treated by the following procedure. The reaction mixture is poured into water, then the reaction mixture is subjected to an extraction with a solvent such as ether, and thereafter the solvent is distilled off from the extract. The so obtained product contains little by-product, and therefore can be used as such for various uses without purification. Of course, it is possible to obtain pure substance by distillation of the above product. It is also possible to separate trans-sabinene oxide and cis-sabinene oxide each other, for example, by employing a thin layer chromatography, column chromatography, a high efficiency fractional distillation and the like.

In the direct synthesis of sabinene oxides by the reaction of 3-isopropyl-2-cyclopenten-1-one with sulfoxonium methylide according to the present invention, the yield of total sabinene oxides consists of the trans-sabinene oxide and cis-sabinene oxide is found in the range of about 58% to 78%, wherein the trans-isomer is produced preferentially. In the synthesis of sabina ketone by the reaction of 3-isopropyl-2-cyclopenten-1-one with sulfoxonium methylide according to the present invention, the yield of sabina ketone is found in the range of 40 to 65%. Furthermore, in the synthesis of sabinene oxide from sabina ketone according to the present invention, the yield of total sabinene oxides including the both trans- and cis-isomers is found in the range of 73 to 98%, wherein the trans-isomer is formed preferentially. Thus, the proportion of trans-isomer to the cis-isomer herein is found in the range of from 55:45 to 82:18, i.e., from about 1.2 to about 4.3.

Thus, according to the present invention, it is possible to produce both trans- and cis-sabinene oxides without substantially any by-products. Also, trans-sabinene oxide is produced preferentially, without any severe condition such as high temperature and high pressure under a mild condition.

The present invention is now further explained in connection with the use of sabinene oxides obtained in the manner described above for preparing sabinene hydrates.

The trans- and cis-sabinene oxides may be separated each other and the trans- and cis-sabinene hydrates are produced separately from these pure isomers. Alternatively, a mixture of the trans- and cis-sabinene oxides is prepared by mixing the once separated pure sabinene oxides in a suitable proportion, the mixture may be employed as starting material. It is further possible to employ, as the starting mixture, the reaction mixture obtained by reacting 3-isopropyl-2-cyclopenten-1-one with sulfoxonium methylide or the reaction mixture which is obtained by reacting sabina ketone with sulfur ylide, both of which contain the trans- and cis-sabinene oxides in a certain ratio. When a mixture of trans- and cis-sabinene oxides is used as the starting material, a mixture of trans- and cis-sabinene hydrates will be formed.

By reducing the sabinene oxides with a reducing agent in an adequate solvent, sabinene hydrates are formed, as shown in the Sequence E.

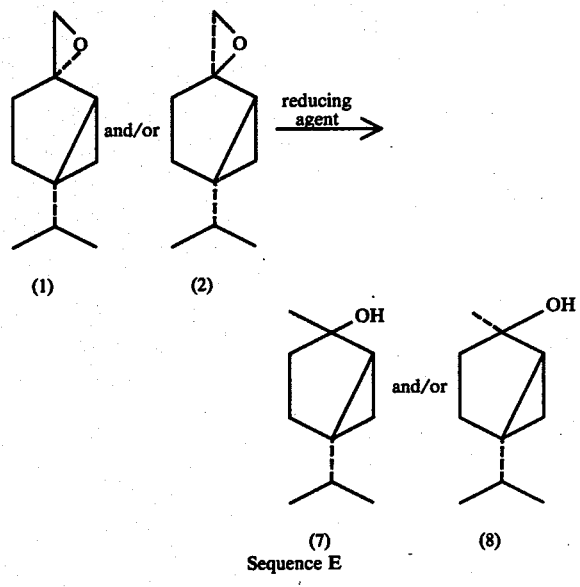

Sequence E

As reducing agent, there can be used metal hydride complexes such as lithium aluminum hydride, lithium trialkoxy aluminum hydride, lithium trialkyl aluminum hydride etc.; metal hydrides such as sodium hydride; metals such as lithium, sodium, sodium-potassium alloy etc.; hydrazines; alkylboranes and the like. Among them, lithium aluminum hydride, lithium trialkoxy aluminum hydride, lithium trialkyl aluminum hydride, lithium, sodium and sodium-potassium alloy are preferable.

As for the solvent, those which are employed in general chemical reactions may be used widely. When a selected solvent system is used depending upon the reducing agent employed, particularly preferable results will be attained. Thus, when the reducing agent is a metal hydride or a metal hydride complex, it is suitable to employ the solvent such as ethyl ether, tetrahydrofuran, bis-(2-methoxyethyl) ether, dimethoxyethane and the like. Also, when the reducing agent is a metal, it is preferable to employ liquid ammonia, lower alkyl amines such as ethylamine, ethylenediamine etc., a mixed solvent consisting of the foregoing with alcohol, and the mixed solvent of hexamethylphosphoric triamide with tert-butyl alcohol etc. It may further be recommended to employ diethylene glycol or triethylene glycol for hydrazines, and bis-(2-methoxyethyl) ether or tetrahydrofuran for diboranes or alkylboranes.

In the reaction of sabinene oxide with a reducing agent, a reaction temperature between −80° C. and 100° C., preferably between 0° C. and 80° C. may be used. When the reaction is conducted at lower temperature, the occurence of side reactions can reliably be prohibited, whereas, when elevated temperature is used, a promotion of the reaction is attained. The reaction time may be from sixty minutes to one day depending upon the molar ratio of sabinene oxide to the reducing agent etc.

As explained previously, the reaction mixture resulted from sabinene oxides is then subjected to an adequate treatment depending upon the reducing agent employed. When either trans- or cis-sabinene oxide is employed alone as the starting material, trans- or cis-sabinene hydrate only will be contained in the product, whereas, if a mixture containing trans- and cis-sabinene oxides at an adequate proportion is used as starting material, then the product will contain substantially both trans- and cis-sabinene hydrates at a proportion depending upon the trans/cis proportion in the starting material. In all cases, however, the product contains little by-product and hence it can be utilized without purification for various uses, such as a component of a flavor or perfume composition. Of course, it is possible to put into practical use after a purification. When trans- and cis-sabinene hydrates are contained in the product, it is also possible to use each isomer separately by isolating the trans- and cis-isomers by means of thin layer chromatography, column chromatography, vacuum distillation, recrystallization or sublimation etc.

The yield of the sabinene hydrates from sabinene oxides is found in the range of about 50 to 92%, and the proportion of trans- sabinene hydrate to cis-sabinene hydrate may vary substantially depending upon the proportion of trans-sabinene oxide to cis-sabinene oxide. Trans-sabinene oxide is contained predominantly in a reaction mixture obtained by reacting 3-isopropyl-2-cyclopenten-1-one with sulfoxonium methylide, a reaction mixture obtained by reacting sabina ketone with sulfoxonium methylide or with sulfonium methylide, or a reaction mixture obtained in such a manner that sabina ketone is first prepared from 3-isopropyl-2-cyclopenten-1-one and is then reacted with sulfoxonium methylide or sulfonium methylide. Therefore, when sabinene hydrates are prepared from the above reaction mixture, trans-sabinene hydrate can be formed in high yield over cis-sabinene hydrate.

As has been described above, it is possible to synthesize the novel compounds only by a single step according to the present invention, by reacting 1 mole of 3-isopropyl-2-cyclopenten-1-one with 2-5 moles of sulfoxonium methylide or, even in the case of taking the course via sabina ketone, by only two steps. In addition, the so obtained novel compounds can be converted into sabinene hydrates simply by reacting them with a reducing agent, so that it has now become possible according to the present invention to synthesize trans- and cis-sabinene hydrates by only two or three steps in an efficient manner. On the contrary, it is necessary to use four steps in the prior process to synthesize the sabinene hydrate from 3-isopropyl-2-cyclopenten-1-one.

Moreover, when sabinene hydrates are produced by reacting sabina ketone with a methyl Grignard reagent in the prior art, trans-sabinene hydrate is scarcely produced. Also, when trans-sabinene hydrate is produced via α-thujene, several steps are required. On the contrary, in the process of reacting 3-isopropyl-2-cyclopenten-1-one with sulfoxonium methylide according to the present invention, trans-sabinene oxide is obtained in higher yield, and hence trans-sabinene hydrate can thus be synthesized in higher yield with only two steps from the starting cyclopentene derivative. It is evident therefore that the present invention attains also an optimum adaptation for synthesizing trans-sabinene hydrate. When sabinene hydrate is prepared through a course via sabina ketone a similar advantage can be obtained.

Also, according to the present invention, when the starting sabinene oxides contain large amount of cis-isomer, it is possible to obtain cis-sabinene hydrate in high yield.

Thus, according to the present invention, trans- and cis-sabinene hydrates can be produced in an efficient manner by simple procedures. In addition, the reaction can be carried out under a mild condition without high temperature and high pressure, and any specific and costly reagent, so that the invention realizes a considerable usefulness in industry.

The following examples are given as specific illustrations of the invention. It should be understood, however, that the invention is not limited to the specific details set forth in the examples.

In the examples, 3-isopropyl-2-cyclopenten-1-one is referred to as "CP".

EXAMPLE 1

To 1.08 g (45 mM) of sodium hydride, 50 ml of dimethylsulfoxide (hereinafter referred to as DMSO) and 10.12 g (46 mM) of trimethylsulfoxonium iodide were added. After stirring for 30 minutes at room temperature, 2.48 g (20 mM) of CP were added dropwise during 3 minutes. After the reaction was carried out for 44 hours at room temperature with stirring, the reaction mixture was poured into ice water and the product was extracted with ether three times. After the extract was washed with water and dried over magnesium sulfate, ether was distilled off. 2.58 g (85% yield) of primary product were obtained.

Through a quantitative analysis by gas chromatography, it was found that the yields of trans- and cis-sabinene oxides (hereinafter referred to as trans-isomer and cis-isomer respectively) were 48% and 30% respectively.

The trans- and cis-isomers were isolated by preparative gas chromatography to determine the physical properties. The results obtained were as follows:

|  | trans-isomer | cis-isomer |
|---|---|---|
| boiling point | 48°–49° C. (2 mmHg) | 57°–58° C. (4 mmHg) |
| elementary analysis | $C_{10}H_{16}O$ | $C_{10}H_{16}O$ |
| C: calculated | 78.89% | 78.89% |

| | trans-isomer | cis-isomer |
|---|---|---|
| found | 78.60% | 78.55% |
| H: calculated | 10.59% | 10.59% |
| found | 10.66% | 10.74% |
| NMR (CCl$_4$, TMS)$\delta$: (ppm) | 0.39 (m, 2H), | 0.42 (m, 2H), |
| | 0.94 (q, 6H), | 0.95 (q, 6H), |
| | 1.15–2.07 (m, 5H), | 1.20–2.05 (m, 5H), |
| | 2.83 (q, 2H), | 2.85 (q, 2H), |
| | 3.80 (m, 1H) | 3.83 (m, 1H) |
| mass spectrum m/e | 152, 137, 123, 121, 109, 81, 67 | 152, 137, 123, 121, 109, 81, 67 |
| GC (PEG 20M, 10%, 2m, 120° C.) | Rt = 6.2 min | Rt = 7.7 min |

Synthesis of Sabinene Hydrates 1.06 g (7 mM) of the thus obtained trans-sabinene oxide were diluted with 30 ml of tetrahydrofuran (hereinafter reffered to as THF). To this solution 0.57 g (15 mM) of lithium aluminum hydride were added portionwise. After heating for 1 hour under reflux, 2.5 ml of water, 10 ml of ether and 1.8 ml of 10% aqueous sodium hydroxide were added in turn under ice cooling, and then the precipitate formed was filtered off. After drying the filtrate over magnesium sulfate, the solvent was distilled off. 0.99 g (92% yield) of trans-sabinene hydrate were obtained. By identification through gas chromatography, mass spectrum and NMR spectrum, it was confirmed that the substance obtained is consistent with the standard product.

Through the same procedure as above, cis-sabinene hydrate was obtained from cis-sabinene oxide in 90% yield.

EXAMPLE 2

To 0.53 g (22 mM) of sodium hydride, 24 ml of N,N-dimethylformamide and 5.06 g (23 mM) of trimethylsulfoxonium iodide were added. After stirring at room temperature for 1 hour, a solution of 1.24 g (10 mM) of CP in 6 ml of N,N-dimethylformamide was poured during 3 minutes, and then the reaction was carried out at room temperature for 35 hours. By treating as described in Example 1, 1.09 g (72% yield) of primary product were obtained. The yields for each of trans- and cis-sabinene oxides were found in 48% and 16% respectively.

Then, to 153 mg (40 mM) of lithium aluminum hydride, 6 ml of 1,2-dimethoxyethane were added under ice cooling. To this solution a solution of 305.3 mg of said mixture of 161.2 mg of trans-sabinene oxide and 56.8 mg of cis-sabinene oxide in 5 ml of 1,2-dimethoxyethane was poured within 5 minutes. After carrying out a reaction at room temperature for 6 hours with stirring, a saturated aqueous sodium sulfate was added to the reaction mixture, then ether was added thereto and the mixture was decanted. The residue was washed with ether and the ether layer was dried over magnesium sulfate. Then, after distilling off the solvent, 176.5 mg of product containing 131 mg (80.4% yield) of trans-sabinene hydrate and 20.1 mg (35.0% yield) of cis-sabinene hydrate were obtained.

EXAMPLE 3

To 0.72 g (30 mM) of sodium hydride 24 ml of THF and 6.82 g (31 mM) of trimethylsulfoxonium iodide were added and the mixture was heated for 6 hours under reflux of THF. Then, a solution of 1.24 g of CP in 6 ml of THF was poured thereinto in 10 minutes and thereafter the mixture was heated for 32 hours at 50° C. Thereafter, same treatments as in Example 1 were carried out. 1.26 g (83% yield) of a primary product were obtained. The yields for each of trans- and cis-sabinene oxides were found in 54% and 21% respectively.

To 153 mg (4.0 mM) of lithium aluminum hydride, 10 ml of ether were added under ice cooling and thereto was poured a solution of 304 mg of said mixture containing 160 mg of trans-sabinene oxide and 56.5 mg of cis-sabinene oxide in 10 ml of ether within 10 minutes. The mixture was heated for 6 hours at room temperature with stirring. The treatments were carried out as described in Example 2. 180.5 mg of a crude product containing 144.4 mg (89.1% yield) of trans-sabinene hydrate and 20.2 mg (35.3% yield) of cis-sabinene hydrate were obtained.

EXAMPLE 4

To 2.64 g (110 mM) of sodium hydride 12.85 g (100 mM) of trimethylsulfoxonium chloride and 150 ml of THF were added and the mixture was heated under reflux for 4 hours with stirring. After cooling the reaction mixture, the by-produced sodium chloride was filtered off using celite as filter aid. A THF solution of dimethylsulfoxonium methylide was obtained. This solution was supplemented to a volume of 200 ml by adding further amount of THF and was stored under nitrogen atmosphere in a refrigerator.

30 ml (15 mM) of the thus prepared solution of dimethylsulfoxonium methylide in THF were placed in a reaction vessel and thereto was added a solution of 0.62 g (5 mM) of CP in 3 ml of THF. The mixture was heated for 30 hours at 50° C. with stirring. Thereafter, same treatments as in Example 1 were carried out. 0.63 g (83% yield) of a primary product were obtained. The yields for each of the trans- and cis-sabinene oxides were found in 55% and 22% respectively.

To 304.4 mg of said mixture product containing 160 mg of trans-sabinene oxide and 56 mg of cis-sabinene oxide, 12 ml of ethylenediamine were added under a nitrogen atmosphere. To this solution, 49 mg of lithium were added under ice cooling and the mixture was stirred vigorously at 35° C. for 3 hours. And then it was cooled to room temperature. To this reaction mixture, ice walter was added and then the product was extracted with THF. After drying the extract over magnesium sulfate, the solvent was distilled off. 280 mg of crude product containing 121 mg (74.6% yield) of trans-sabinene hydrate and 22.1 mg (38.8% yield) of cis-sabinene hydrate were obtained.

EXAMPLE 5

5 ml of n-hexane, 2.53 g (23 mM) of trimethylsulfoxonium iodide and 10 ml of DMSO were added to 6.7 ml (11 mM) of 15% solution of n-butyllithium in n-hexane and the mixture was stirred for 35 minutes. To this mixture a solution of 0.62 g (5 mM) of CP in 5 ml of DMSO was poured within 5 minutes and the reaction was carried out at room temperature for 23 hours. Thereafter, the same treatments as in Example 1 were carried out. 0.47 g (62% yield) of a primary product were obtained. The yields for the trans- and cis-isomers were found in 47% and 11% respectively.

By reducing the so obtained trans- and cis-sabinene oxides as described in Example 1, trans- and cis-sabinene hydrates were obtained in high yield.

EXAMPLE 6

10 ml of DMSO and 3.19 g (14.5 mM) of trimethylsulfoxonium iodide were added to 1.57 g (14 mM) of potassium tert-butoxide and the mixture was stirred for 25 minutes at room temperature. Subsequently, 0.62 g (5 mM) of CP were poured thereto within 1 minute, further 10 ml of DMSO were added and reaction was carried out for 24 hours. The treatments were carried out as described in Example 1. 0.51 g (67% yield) of sabinene oxides were obtained. The yields for trans- and cis-sabinene oxides were found in 40% and 21% respectively.

The so obtained trans- and cis-sabinene oxides were reduced as described in Example 1. Trans- and cis-sabinene hydrates were obtained in high yield.

EXAMPLE 7

20 ml of DMSO and 2.72 g (11.5 mM) of (dimethylamino)dimethylsulfoxonium fluoroborate were added to 0.26 g (11 mM) of sodium hydride and the mixture was stirred for 25 minutes at room temperature. Then, 0.62 g (5 mM) of CP were poured thereto in 5 minutes and the reaction was carried out at 50° C. for 20 hours. The treatments were carried out as described in Example 1. 0.59 g (78% yield) of a primary product were obtained. Yields for trans- and cis-sabinene oxides were found in 42% and 21% respectively.

The so obtained trans- and cis-sabinene oxides were reduced as described in Example 1. The trans- and cis-Sabinene hydrates were obtained in high yield.

EXAMPLE 8

20 ml of DMSO and 5.06 g (23 mM) of trimethylsulfoxonium iodide were added to 0.53 g (22 mM) of sodium hydride, the mixture was stirred for 25 minutes at room temperature, and then 2.48 g (20 mM) of CP were poured to the mixture in 5 minutes. Then, 8 ml of DMSO were further added and the reaction was carried out in such a manner that the mixture was stirred at room temperature for 2.5 hours and then at 65° C. for 2 hours and 15 minutes. Thereafter, the reaction mixture was poured into ice water and then the product was extracted with ether three times. The extract was washed with water and dried over magnesium sulfate. After distilling off the ether, 240 g (87% yield) of crude product were obtained, from which 1.45 g (52% yield) of sabina ketone were obtained by a vacuum distillation. It was found that this sabina ketone boiled at 76°–78° C. (7 mmHg) and that the results of determinations of IR, NMR, MS and GC coincided completely with the standard substance synthesized separately.

Next, 20 ml of DMSO and 2.53 g (11.5 mM) of trimethylsulfoxonium iodide were added to 0.26 g (11 mM) of sodium hydride, the mixture was stirred for 20 minutes at room temperature and then thereto was poured a solution of 1.38 g (10 mM) of the sabina ketone in 10 ml of DMSO within 5 minutes. Thereafter, the reaction was carried out in such a way that the mixture was stirred at room temperature for 15 minutes and then at 50° C. for 8 hours. Then, the reaction mixture was poured into ice water and the product was extracted with ether three times. The extract was washed with water, dried over magnesium sulfate, and ether was distilled off. 1.46 g (96% yield) of a primary product were obtained.

By analysing the so obtained product quantitatively through gas chromatography, the yields for trans- and cis-sabinene oxides were found in 52% and 34% respectively.

The results of the physical properties observed for each of the trans- and cis-isomers isolated by a preparative gas chromatography were summarized as follows:

|  | trans-isomer | cis-isomer |
| --- | --- | --- |
| boiling point | 48°–49° C. (2 mmHg) | 57°–58° C. (4 mmHg) |
| elementary analysis | $C_{10}H_{16}O$ | $C_{10}H_{16}O$ |
| C: calculated | 78.89% | 78.89% |
| found | 78.60% | 78.55% |
| H: calculated | 10.59% | 10.59% |
| found | 10.66% | 10.74% |
| NMR ($CCl_4$, TMS)δ(ppm) | 0.39 (m, 2H), | 0.42 (m, 2H), |
|  | 0.94 (q, 6H), | 0.95 (q, 6H), |
|  | 1.15–2.07 (m, 5H), | 1.20–2.05 (9m, 5H), |
|  | 2.83 (q, 2H), | 2.85 (q, 2H), |
|  | 3.80 (m, 1H), | 3.83 (m, 1H), |
| mass spectrum m/e | 152, 137, 123, | 152, 137, 123, 121, |
|  | 121, 109, 81, 67 | 109, 81, 67 |
| GC (PEG 20M, 10%, 2m, 120° C.) | Rt = 6.2 min | Rt = 7.7 min |

Synthesis of Sabinene Hydrates 1.06 g (7 mM) of the trans-sabinene oxide synthesized as above were diluted with 30 ml of THF and thereto were mixed 0.57 g (15 mM) of lithium aluminum hydride portionwise. After heating for 1 hour under reflux, 2.5 ml of water, 10 ml of ether and 1.8 ml of 10% aqueous sodium hydroxide were added in turn to the mixture under ice cooling. Then, by removing the precipitate by filtration, drying the filtrate over magnesium sulfate and distilling off the solvent, 0.99 g (92% yield) of trans-sabinene hydrate were obtained. Through identification by gas chromatography, mass spectrum and nuclear magnetic resonance spectrum, it was confirmed that the substance obtained as above coincided with the standard material.

Also, by operating in same manner as above, cis-sabinene hydrate was obtained in about 90% yield.

EXAMPLE 9

Sanina ketone was synthesized as described in Example 8. 1.38 g of sabina ketone (50% yield) were obtained.

15 ml of DMSO were added to 0.36 g (15 mM) of sodium hydride and the mixture was stirred at 60°–70° C. for 45 minutes to synthesize dimusylsodium. To this dimusyl sodium 15 ml of THF were added and the mixture was cooled to 0° C. Thereafter, 2.91 g (15.5 mM) of trimethylsulfonium methylsulfate and then a solution of 1.38 g (10 mM) of said sabina ketone in 7 ml of DMSO were added thereto. Thereafter, the reaction was carried out at 0° C. for 30 minutes and then at room temperature for 4 hours. The treatments were carried out as described in Example 8. 1.34 g (88% yield) of a primary product were obtained. The yields for trans- and cis-sabinene oxides were found in 48% and 35% respectively.

Then, 15 ml of 1,2-dimethoxyethane were added under ice cooling to 383 mg (10 mM) of lithium aluminum hydride and thereto was further added dropwise a solution of 0.76 g of said mixture of trans- and cis-sabinene oxides containing 0.40 g of trans-isomer and 0.14 g of cis-isomer in 12 ml of 1,2-dimethoxyethane within 5 minutes. After reacting at room temperature for 6 hours with stirring, a saturated aqueous sodium sulfate was added to the reaction mixture, then ether was added and the mixture was decanted. The residue was washed with ether and the ether layer was dried over magnesium sulfate. Then, the solvent was distilled off. 0.44 g of a crude product which contain 0.33 g (80.4% yield) of trans-sabinene hydrate and 0.05 g (35.0% yield) of cis-sabinene hydrate were obtained.

EXAMPLE 10

To 0.52 g (22 mM) of sodium hydride 40 ml of DMSO and 5.06 g (23.0 mM) of trimethylsulfoxonium iodide were added and the mixture was stirred at room temperature for 3.5 hours. This reaction mixture was then poured dropwise into a solution of 2.48 g (20 mM) of CP in 20 ml of DMSO during 6 hours at 50° C. Then, the reaction was carried out for 2 hours at 50° C. with stirring. Subsequently, the treatments were carried out as described in Example 8. 2.54 g (92% yield) of crude product were produced, from which 1.70 g (62% yield) of sabina ketone were obtained by distillation.

Then, to 0.36 g (15 mM) of sodium hydride 20 ml of N,N-dimethylformamide and 3.41 g (15.5 mM) of trimethylsulfoxonium iodide were added and the mixture was stirred at room temperature for 20 minutes. Thereto was then poured a solution of 1.38 g (10 mM) of the sabina ketone in 10 ml of N,N-dimethylformamide dropwise in 5 minutes, and the reaction was carried out at room temperature for 1 hour and then at 50° C. for 6 hours. Thereafter, the treatments were carried out in the same manner as described in Example 8. 1.16 g (76% yield) of a primary product were obtained. The yields of trans-isomer and cis-isomer were found in 46% and 27% respectively.

Next, a reaction mixture was formed by adding 25 ml of ether to 0.38 g (10 mM) of lithium aluminum hydride under ice cooling and further adding thereto dropwise a solution of 0.76 g of said mixture of 0.40 g of trans-sabinene oxide and 0.14 g of cis-sabinene oxide in 25 ml of ether within 10 minutes. After reacting at room temperature for 6 hours with stirring, the treatments were carried out as described in Example 9. A crude product was obtained in an amount of 0.45 g, in which 0.36 g (89.1% yield) of trans-sabinene hydrate and 0.05 g (35.3% yield) of cis-sabinene hydrate were contained.

EXAMPLE 11

Sabina ketone was synthesized as described in Example 10. 1.25 g (91% yield) of crude product containing 68% of sabina ketone were obtained.

To 0.8 g (7 mM) of potassium tert-butoxide 10 ml of DMSO and 1.60 g (7.25 mM) of trimethylsulfoxonium iodide were added and the mixture was stirred at room temperature for 20 minutes. To this reaction mixture a solution of 1.01 g of said crude product (sabina ketone 0.69 g, 5 mM) in 5 ml of DMSO was then poured dropwise during 5 minutes, and thereafter the reaction was carried out at room temperature for 17 hours and then at 50° C. for 6.5 hours. The treatments were carried out as described in Example 8. 0.67 g (97% yield) of a primary product were obtained. The yields for trans- and cis-sabinene oxides were found in 51% and 31% respectively.

Then, 0.61 g of said mixture of 0.32 g of trans-sabinene oxide and 0.11 g of cis-sabinene oxide were mixed with 24 ml of ethylenediamine under nitrogen atmosphere, and to this mixture 0.10 g of lithium were added under ice cooling. This mixture was stirred vigorously at 35° C. for 3 hours, and then cooled to room temperature. Ice water was added to the reaction mixture, and the product was extracted with THF. The extract was dried over magnesium sulfate and THF was distilled off. A crude product was obtained in an amount of 0.56 g, in which 0.24 g (74.6% yield) of trans-sabinene hydrate and 0.04 g (38.8% yield) of cis-sabinene hydrate were contained.

EXAMPLE 12

90 ml of N,N-dimethylformamide and 7.59 g (34.5 mM) of trimethylsulfoxonium iodide were added to 0.78 g (33 mM) of sodium hydride and the mixture was stirred at room temperature for 1.5 hours. After this reaction mixture was diluted with 45 ml of N,N-dimethylformamide, the mixture was poured dropwise into a solution of 3.72 g (30 mM) of CP in 30 ml of N,N-dimethylformamide during 4 hours at 50° C., and then reaction was carried out at 50° C. for 3 hours. Thereafter, by treating as described in Example 8, a crude product was obtained in an amount of 3.12 g (75% yield); from which 1.92 g (47% yield) of sabina ketone were obtained by distillation.

Then, 10 ml of DMSO, 15 ml of benzene, 10 ml of isopropyl alcohol, 1.38 g (10 mM) of sabina ketone, 1.60 g (20 mM) of 50% aqueous sodium hydroxide and 2 ml of water were added to 4.40 g (20 mM) of trimethylsulfoxonium iodide, and the reaction was carried out at room temperature for 15 minutes and then at 50° C. for 6 hours. By treating as described in Example 8, a primary product was obtained in an amount of 1.50 g (99% yield). The yields for trans- and cis-sabinene oxides were found in 57% and 35% respectively.

By treating the so obtained trans- and cis-sabinene oxides as described in Example 8, trans- and cis-sabinene hydrates were obtained in high yield.

EXAMPLE 13

To 10.2 ml (16.5 mM) of 15% solution of n-butyllithium in n-hexane, 15 ml of n-hexane, 3.81 g (17.25 mM) of trimethylsulfoxonium iodide and 30 ml of DMSO were added and the mixture was stirred for 30 minutes. This reaction mixture was poured dropwise into a solution of 1.86 g (15 mM) of CP in 15 ml of DMSO in 4 hours. After reacting for two hours at room temperature, the treatments were carried out as described in Example 8. 1.29 g (62% yield) of a primary product were produced, from which 0.87 g (43% yield) of sabina ketone were obtained by distillation.

Then, 12.85 g (100 mM) of trimethylsulfoxonium chloride and 150 ml of THF were added to 2.64 g (110 mM) of sodiumm hydride and the mixture was heated under reflux for 4 hours with stirring. After the reaction mixture was cooled, the by-produced sodium chloride was filtered off by using celite as filter aid. A THF solution of dimethylsulfoxonium methylide was obtained. This solution was supplemented to an amount of 200 ml by adding further THF and was stored in a refrigerator under nitrogen atmosphere.

14 ml (7 mM) of the above THF solution of dimethylsulfoxonium methylide were placed in a reaction vessel. To this solution a solution of 0.69 g (5 mM) of said sabina ketone in 5 ml of THF was added, and the reaction was carried out at room temperature for 1 hour and then at 50° C. for 5 hours with stirring. The treatments were carried out as described in Example 8. 0.70 g (92% yield) of primary product were obtained. The yields for trans-sabinene oxide and cis-sabinene oxide were found in 64% and 24% respectively.

By reducing the so obtained trans- and cis-sabinene oxides as described in Example 8, trans- and cis-sabinene hydrates were obtained in high yield.

EXAMPLE 14

To a THF solution of lithium diisopropylamide prepared from 26 mM of diisopropylamine and 26 mM of n-butyllithium, 6.16 g (28 mM) of trimethylsulfoxonium iodide were added under ice cooling, and the mixture was stirred at 0° C. for 30 minutes and then at room temperature for 2 hours. This reaction mixture was poured dropwise into a solution of 2.48 g (20 mM) of CP in 20 ml of THF during 4 hours. After the reaction was carried out at room temperature for 3 hours, the treatments were carried out as described in Example 8. 2.48 g (89% yield) of crude product were produced, from which 1.76 g (63% yield) of sabina ketone were obtained by distillation.

Then, 20 ml of THF and 3.41 g of trimethylsulfoxonium iodide were added to 0.36 g of sodium hydride and the reaction was carried out for 4 hours under the reflux of THF. Subsequently, a solution of 1.38 g of the sabina ketone in 10 ml of THF was poured thereto in 5 minutes, and thereafter the reaction was carried out for 16 hours at room temperature and then for 6 hours at 64° C. The treatments were carried out as described in Example 8. 1.50 g (99% yield) of primary product were obtained. The yields of trans- and cis-sabinene oxides were found in 62% and 23% respectively.

The so obtained trans- and cis-sabinene oxides were reduced as described in Example 8. Trans- and cis-sabinene hydrates were obtained in high yield.

EXAMPLE 15

60 ml of DMSO and 5.08 g (23 mM) of trimethylsulfoxonium iodide were added to 2.48 g (22 mM) of potassium tert-butoxide and the mixture was stirred for 20 minutes at room temperature. This reaction mixture was poured dropwise into a solution of 2.48 g (20 mM) of CP in 20 ml of DMSO during 3 hours and the reaction was carried out at room temperature for 30 minutes. The treatments were carried out as described in Example 8. 2 g (73% yield) of crude product were produced, from which 1.41 g (51% yield) of sabina ketone were obtained by distillation.

Then, 0.26 g (11 mM) of sodium hydride, 20 ml of DMSO and 2.72 g (11.5 mM) of (diethylamino)dimethylsulfoxonium fluoroborate were mixed and the mixture was stirred at room temperature for 20 minutes. Thereafter, a solution of 1.38 g (10 mM) of sabina ketone in 10 ml of DMSO was poured thereto dropwise during 5 minutes. After reacting at room temperature for 15 minutes and then at 50° C. for 4 hours, the treatments were carried out as described in Example 8. 1.38 g (91% yield) of primary product were obtained. The yields for trans-sabinene oxide and cis-sabinene oxide were found in 52% and 32% respectively.

By reducing the so obtained trans- and cis-sabinene oxide as described in Example 8, trans- and cis-sabinene hydrates were obtained in high yield.

EXAMPLE 16

25 ml of DMSO, 35 ml of benzene, 25 ml of isopropyl alcohol, 3.1 g (25 mM) of CP, 2.4 g (30 mM) of 50% aqueous sodium hydroxide and 5 ml of water were added to 6.9 g (31.25 mM) of trimethylsulfoxonium iodide and the reaction was carried out at room temperature for 5 hours. Then, the treatments were carried out as described in Example 8. 2.6 g (76% yield) of crude product were produced, from which 1.45 g (42% yield) of sabina ketone were obtained by distillation.

0.36 g (15 mM) of sodium hydride and 15 ml of DMSO were mixed and the mixture was stirred at 60°–70° C. for 45 minutes to synthesize dimusyl sodium. 15 ml of THF were added thereto and the mixture was cooled to 0° C. Thereafter, 3.50 g (15.5 mM) of dimethylphenylsulfonium fluoroborate and then solution of 1.38 g (10 mM) of said sabina ketone in 7 ml of DMSO were added thereto, and the reaction was carried out at 0° C. for 10 minutes and then at room temperature for 1 hour and 40 minutes. Extraction operation was carried out as described in Example 8 and the extract was subjected to a fractional distillation under reduced pressure. 1.28 g (84% yield) of a fraction containing the trans- and cis-isomers were obtained. By the quantitative analysis thereof through gas chromatography, it was determined that the yields for trans-sabinene oxide and cis-sabinene oxide were found in 48% and 30% respectively.

By reducing the so obtained trans- and cis-sabinene oxides as described in Example 8, trans- and cis-sabinene hydrates were obtained in high yield.

EXAMPLE 17

44 ml (22 mMM) of this THF solution of dimethylsulfoxonium methylide obtained in Example 13 were placed in a dropping funnel and dropped into a solution of 2.48 g (20 mM) of CP in 20 ml of THF at 50° C. during 6 hours. Thereafter, the mixture was stirred at 50° C. for 2 hours to carry out the reaction. The treatments were carried out as described in Example 8. 2.44 g (88% yield) of crude product were produced, from which 1.68 g (60% yield) of sabina ketone were obtained by distillation.

The treatments were carried out as described in Example 16 except that 5.43 g (15.5 mM) of methyl(m-nitrophenyl)phenylsulfonium perchlorate were employed instead of dimethylphenylsulfonium fluoroborate and that the reaction after the addition of sabina ketone was carried out at 0° C. for 30 minutes and then at room temperature for 3 hours. 1.29 g (85% yield) of a fraction containing trans- and cis-sabinene oxides were obtained. The yields for the trans- and cis-isomers were found in 51% and 31% respectively.

By reducing the so obtained trans- and cis-sabinene oxides as described in Example 8, trans- and cis-sabinene hydrates were obtained in high yield.

EXAMPLE 18

THF solution of dimethylsulfoxonium methylide was reacted with CP as described in Example 17. Reaction mixture obtained was used for the following reaction without any isolation and purification.

15 ml of n-hexane, 3.41 g (15.5 mM) of trimethylsuloxonium iodide and 10 ml of DMSO were added to 9.2 ml (15 mM) of 15% solution ofn-butyllithium in n-hexane and the mixture was stirred for 25 minutes. To this mixture said reaction mixture containing sabina ketone was poured dropwise and the reaction was carried out at room temperature for 16 hours and then at 50° C. for 1 hour. The treatments were carried out as described in Example 8. 1.52 g (about 100% yield) of primary product were obtained. The yields for trans-sabinene oxide and cis-sabinene oxide were found in 54% and 34% respectively.

The so obtained trans- and cis-sabinene oxides were reduced as described in Example 8. Trans- and cis-sabinene hydrates were obtained in high yield.

EXAMPLE 19

60 ml of DMSO and 5.44 g (23 mM) of (diethylamino)dimethylsulfoxonium fluoroborate were added to 0.52 g (22 mM) of sodium hydride and the mixture was stirred at room temperature for 20 minutes. This reaction mixture was poured dropwise into a solution of 2.48 g (20 mM) of CP in 20 ml of DMSO at 50° C. for 3 hours. Then, after the reaction was carried out at 50° C. for 1 hour, the treatments were carried out as described in Example 8. 2.40 g (86% yield) of crude product were produced, from which 1.65 g (60% yield) of sabina ketone were obtained by distillation.

The treatments were carried out as described in Example 16 except that 4.51 g (15.5 mM) ofmethyldiphenylsulfonium perchlorate were employed in the place of dimethylphenylsulfonium fluoroborate and that the condition of reaction after the addition of sabina ketone was changed to 0° C., 1 hour followed by room temperature, 2 hours. 1.37 g (90% yield) of a fraction containing trans- and cis-sabinene oxides were obtained. The yields for trans- and cis-isomers were found in 54% and 34% respectively.

By reducing the so obtained trans- and cis-sabinene oxides as described in Example 8, trans- and cis-sabinene hydrates were obtained in high yield.

EXAMPLE 20

To 0.36 g (15 mM) of sodium hydride 20 ml of N,N-dimethylformamide and 3.41 g (15.5 mM) of trimethylsulfoxonium iodide were added and the mixture was stirred at room temperature for 20 minutes. Thereto was then poured a solution of 1.38 g (10 mM) of the sabina ketone in 10 ml of N,N-dimethylformamide dropwise in 5 minutes, and the reaction was carried out at room temperature for 1 hour and then at 50° C. for 6 hours. Thereafter, the treatments were carried out in the same manner as described in Example 8. 1.16 g (76% yield) of a primary product were obtained. The yields of trans- isomer and cis-isomer were found in 46% and 27% respectively.

Trans- and cis-sabinene oxides were isolated by a preparative gas chromatography.

Then, 6 ml of THF were added under ice cooling to 153 mg (4.0 mM) of lithium aluminum hydride and thereto was further added dropwise a solution of 161.2 mg of trans-sabinene oxide in 5 ml of 1,2-dimethoxyethane within 5 minutes. After reacting at room temperature for 6 hours with stirring, a saturated aqueous sodium sulfate was added to the reaction mixture. Then ether was added and the product was decanted. The residue was washed with ether and the ether layer was dried over magnesium sulfate. Then, the solvent was distilled off. 131 mg (80.4% yield) of trans-sabinene hydrate were obtained.

Also, 95 mg of cis-sabinene oxide was reduced with lithium aluminum hydride in same manner. 33 mg (35% yield) of cis-sabinene hydrate were obtained.

EXAMPLE 21

12.85 g (100 mM) of trimethylsulfoxonium chloride and 150 ml of THF were added to 2.64 g (110 mM) of sodium hydride and the mixture was heated under reflux for 4 hours with stirring. After the reaction mixture was cooled, the by-produced sodium chloride was filtered off by employing celite as filter aid. A THF solution of dimethylsulfoxonium methylide was obtained. This solution was supplemented to an amount of 200 ml by adding further THF and was stored in a refrigerator under nitrogen atmosphere.

28 ml (14 mM) of the above THF solution of dimethylsulfoxonium methylide were added to a solution of 1.38 g (10 mM) of sabina ketone in 10 ml of THF, and the reaction was carried out at room temperature for 1 hour and then at 50° C. for 5 hours with stirring. The treatments were carried out as described in Example 8. 1.40 g (92% yield) of primary product were obtained. The yields for trans-sabinene oxide and cis-sabinene oxide were found in 64% and 24% respectively.

Then, 304.4 mg of said mixture of 160 mg of trans-sabinene oxide and 56 mg of cis-sabinene oxide were mixed with 12 ml of ether, and the resulting reaction mixture was mixed with 170 mg of lithium aluminum hydride under ice cooling. This mixture was stirred vigorously at 35° C. for 3 hours, and then cooled to room temperature. After adding ice water to the reaction mixture and extracting with THF, the extract was dried over magnesium sulfate and THF was distilled off. A crude product was obtained in an amount of 280 mg, in which 121 mg (74.6% yield) of trans-sabinene hydrate and 22.1 mg (38.8% yield) of cis-sabinene hydrate were contained.

EXAMPLE 22

Under ice cooling 3.41 g (15.5 mM) of trimethylsulfoxonium iodide were added to a THF solution of lithium diisopropyl amide which was prepared from 15 mM of diisopropylamine and 15 mM of n-butyl lithium. After the mixture was stirred at 0° C. for 25 minutes and then at room temperature for 2.5 hours, a solution of 1.38 g (10 mM) of sabina ketone in 10 ml of THF was poured dropwise thereto. After the reaction was carried out at room temperature for 3 hours, the treatments were carried out as described in Example 8. 1.49 g (98% yield) of sabinene oxides were obtained. The yields for trans- and cis-sabinene oxides were found in 55% and 36% respectively.

Then, Example 8 was repeated with the exception that trans- and cis-sabinene oxides were reduced in 1,2-dimethoxyethane instead of THF. Trans- and cis-sabinene hydrates were obtained in high yield.

EXAMPLE 23

Dimusyl sodium was synthesized by mixing 0.31 g (13 mM) of sodium hydride and 15 ml of DMSO and heating at 60°–70° C. for 45 minutes with stirring. To this dimusyl sodium 15 ml of THF were added and then the mixture was cooled to 0° C. Thereafter, 2.75 g (13.5 mM) of trimethylsulfonium iodide and then solution of 1.38 g (10 mM) of sabina ketone in 7 ml of DMSO were added thereto, and the reaction was carried out for 30 minutes at 0° C. and then for 3 hours at room temperature. The treatments were carried out as described in Example 8. 1.50 g (99% yield) of sabinene oxides were obtained. The yields for trans- and cis-sabinene oxides were found in 60% and 38% respectively.

Then, Example 8 was repeated with the exception that trans- and cis-sabinene oxides were reduced with lithium in ethylenediamine. Trans- and cis-sabinene hydrates were obtained in high yield.

EXAMPLE 24

3.50 g (15.5 mM) of dimethylphenylsulfonium fluoroborate and 1.38 g (10 mM) of sabina ketone were diluted with 15 ml of DMSO and 15 ml of THF. After cooling to 0° C., 0.36 g (15 mM) of sodium hydride were added thereto with stirring. After the reaction was carried out at 0° C. for 1 hour and then at room temperature for 4 hours, the treatments were carried out as described in Example 16. 1.46 g (96% yield) of a fraction containing trans- and cis-isomers were obtained. The yields for trans- and cis-sabinene oxides were found in 59% and 34% respectively.

By reducing the so obtained trans- and cis-sabinene oxides as described in Example 8, trans- and cis-sabinene hydrates were obtained in high yield.

EXAMPLE 25

The treatments were carried out as described in Example 16 except that 3.91 g (15.5 mM) of dimethyl(m-tolyl)sulfonium perchlorate were employed instead of dimethylphenylsulfonium fluoroborate and that the reaction after the addition of sabina ketone was carried out at 0° C. for 30 minutes and then at room temperature for 2 hours. 1.35 g (89% yield) of a fraction containing trans- and cis-sabinene oxides were obtained. The yields for the trans- and cis-isomers were found in 54% and 32% respectively.

By reducing the so obtained trans- and cis-sabinene oxides as described in Example 8, trans- and cis-sabinene hydrates were obtained in high yield.

EXAMPLE 26

The treatments were carried out as described in Example 16 except that 5.97 g (15.5 mM) of (p-chlorophenyl)methyl(p-nitrophenyl)sulfonium perchlorate were used instead of dimethylphenylsulfonium fluoroborate and that the reaction after the addition of sabina ketone was carried out at 0° C. for 30 minutes and then at room temperature for 2 hours. 1.26 g (83% yield) of a fraction containing trans- and cis-sabinene oxides were obtained. The yields for the trans- and cis-isomers were found in 49% and 30% respectively.

By reducing the so obtained trans- and cis-sabinene oxides as described in Example 8, trans- and cis-sabinene hydrates were obtained in high yield.

Several Formulation Examples in which the novel compound trans- or cis-sabinene oxide of the present invention in formulated in various perfume or flavor compositions are given.

Formulation Example 1

Spearmint type flavor composition for dentifrice

| Spearmint oil | 350 | parts by weight |
|---|---|---|
| Carvone | 100 | " |
| Peppermint oil | 220 | " |
| Menthol | 150 | " |
| Anethole | 120 | " |
| Lemon oil | 40 | " |
| Eugenol | 10 | " |
| Clove oil | 3 | " |
| trans-Sabinene oxide | 5 | " |
| Ethanol | 2 | " |
| | 1000 | " |

This flavor composition exhibits a flavorousness, in which the fragrance tone of spearmint is elevated and the refreshing as well as refrigerant feels are increased as compared to composition without trans-sabinene oxide, so that the odorant efficiency is increased.

Formulation Example 2

Peppermint type flavor composition for dentifrice
The following flavor composition was formulated in a usual manner:

| Peppermint oil | 640 | parts by weight |
|---|---|---|
| Menthol | 130 | " |
| Anethole | 120 | " |
| Menthyl acetate | 20 | " |
| Clove oil | 15 | " |
| Menthone oil | 40 | " |
| Cinnamon oil | 2 | " |
| Vanilla tincture | 20 | " |
| Orange oil | 5 | " |
| trans-Sabinene oxide | 7 | " |
| Ethanol | 1 | " |
| | 1000 | " |

This flavor composition had a flavorousness, in which the oily odor originated from terpene was reduced as compared to composition without trans-sabinene oxide and showed an effect of making mild and fresh so as to offer a bracing feel in the mouth.

Formulation Example 3

Perfume composition Jasmine Floral
The following perfume composition was formulated in a usual manner:

| Benzyl acetate | 200 | parts by weight |
|---|---|---|
| Rose P (Phenyl ethyl alcohol) | 200 | " |
| Linalool | 100 | " |
| Hydroxy citronellal | 300 | " |
| Geranyl acetate | 60 | " |
| Ethyl cinnamate | 10 | " |
| Ylang-ylang oil No. 1 | 70 | " |
| Hexyl cinnamic aldehyde | 50 | " |
| Aldehyde $C_{14}$ | 5 | " |
| trans-Sabinene oxide | 5 | " |
| | 1000 | " |

This flavor composition exhibited a greenish fresh fragrance inherent to the Absolute Jasmine.

Formulation Example 4

Lavender type perfume composition for household products

The following flavor composition was formulated in usual way:

| | | |
|---|---|---|
| Bornyl acetate | 130 | parts by weight |
| Benzyl acetate | 120 | " |
| Benzyl benzoate | 130 | " |
| Linalyl acetate | 130 | " |
| Amyl cinnamic aldehyde | 50 | " |
| Coumarin | 50 | " |
| Lavandine oil | 30 | " |
| Orange oil | 130 | " |
| Cyclamen aldehyde | 30 | " |
| Geraniol | 30 | " |
| Musk ambrette | 20 | " |
| Velonate (p-tert-Butylcyclohexyl acetate) | 80 | " |
| trans-Sabinene oxide | 70 | " |
| | 1000 | " |

While perfumes for household products require especially a refreshing feel in practical service, the above recited perfume composition with trans-sabinene oxide attains an effect of intensifying the refreshing feel and exhibiting fresh feel as contrasted to that without trans-sabinene oxide.

Formulation Example 5

Spearmint type flavor composition for dentifrice
The following flavor composition was formulated in usual procedure.

| | | |
|---|---|---|
| Spearmint oil | 350 | parts by weight |
| Carvone | 100 | " |
| Peppermint oil | 220 | " |
| Menthol | 150 | " |
| Anethole | 120 | " |
| Lemon oil | 30 | " |
| Eugenol | 10 | " |
| Clove oil | 3 | " |
| cis-Sabinene oxide | 15 | " |
| Ethanol | 2 | " |
| | 1000 | " |

This flavor composition was characterized by the flavorousness in which the flavor tone of spearmint was accentuated and at the same time the flavor became refrigerant due to the increase of the refrigerant feel as compared to composition without cis-sabinene oxide, so that the composition had approved a marked advantage for flavor.

Formulation Example 6

Peppermint type flavor composition for dentifrice
The following flavor composition was formulated in usual manner:

| | | |
|---|---|---|
| Peppermint oil | 640 | parts by weight |
| Menthol | 130 | " |
| Anethole | 120 | " |
| Menthyl acetate | 20 | " |
| Clove oil | 15 | " |
| Menthone oil | 50 | " |
| Cinnamone leaf oil | 2 | " |
| Vanilla tincture | 10 | " |
| Orange oil | 5 | " |
| cis-Sabinene oxide | 17 | " |
| Ethanol | 1 | " |
| | 1000 | " |

This flavor composition attains an effect of removing the oily odor inherent to Japanese mints and at the same time improving the bitterish fragrant of menthol, as compared to that without cis-sabinene oxide.

Formulation Example 7

Perfume composition Fantasy Floral
The following perfume composition was formulated in a usual manner:

| | | |
|---|---|---|
| Ethyl vanillin | 15 | parts by weight |
| Heliotropin | 150 | " |
| Neroli Bigarade | 150 | " |
| Tuberose base | 50 | " |
| Jasmine base | 75 | " |
| Aldehyde C9 10%-soln. | 5 | " |
| Hydroxy citronellal | 150 | " |
| Phenyl ethyl alcohol | 100 | " |
| Jonquil base | 45 | " |
| Clove oil | 25 | " |
| Ylang oil | 300 | " |
| Rhodinol | 90 | " |
| cis-Sabinene oxide | 415 | " |
| Vanillin 5% soln. | 2000 | " |
| Aldehyde C14 50% soln. | 5 | " |
| Hyacinth base | 180 | " |
| Musk ambrette 15% soln. | 150 | " |
| Musk ketone 15% Soln. | 250 | " |
| | 4155 | " |

This perfume composition reveals an effect of imparting to the floral fragrant of Sweet pea with refreshing and fresh tones.

Formulation Example 8

Perfume composition White Rose
The following perfume composition was formulated in usual manner:

| | | |
|---|---|---|
| Ethyl vanillin | 2 | parts by weight |
| Heliocrat | 4 | " |
| Musk ambrette | 30 | " |
| Musk ketone | 20 | " |
| Rhodinol | 85 | " |
| Bois-de-rose oil | 100 | " |
| Phenyl ethyl alcohol | 450 | " |
| Aldehyde C8 10% soln. | 50 | " |
| cis-Sabinene oxide | 160 | " |
| Rose base | 99 | " |
| | 1000 | " |

This perfume composition exhibits an effect in which the fragrance of White Rose is made brilliant and fresh.

Thus, the invention has been described with reference to preferred embodiments, however, it is to be understood that variations and modifications may be resorted to as will be apparent to those skilled in the art. Such variations and modifications are to be considered within the purview and scope of the claims appended hereto.

What is claimed is:
1. Spiro[5-isopropylbicyclo[3.1.0]hexane-2,2′-oxiranes].

2. Spiro[5-isopropylbicyclo[3.1.0]hexane-2,2'-oxirane] according to claim 1, wherein it represents the trans-isomer having the chemical structural formula:
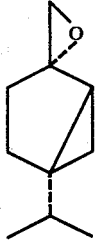
3. Spiro[5-isopropylbicyclo[3.1.0]hexane-2,2'-oxirane] according to claim 1, wherein it represents the cis-isomer having the chemical structural formula:
* * * * *